(12) United States Patent
Matsubara et al.

(10) Patent No.: US 9,052,320 B2
(45) Date of Patent: Jun. 9, 2015

(54) METHOD FOR ANALYSIS OF HEPATITIS B VIRUS S ANTIGEN

(75) Inventors: Naoko Matsubara, Wako (JP); Yasuhiro Sugamata, Wako (JP); Osamu Kusano, Wako (JP); Noriko Shirata, Wako (JP)

(73) Assignee: Advanced Life Science Institute, Inc., Wako-shi (JP)

( * ) Notice: Subject to any disclaimer, the term of this patent is extended or adjusted under 35 U.S.C. 154(b) by 786 days.

(21) Appl. No.: 12/447,806

(22) PCT Filed: Oct. 30, 2007

(86) PCT No.: PCT/JP2007/071150
§ 371 (c)(1),
(2), (4) Date: Apr. 29, 2009

(87) PCT Pub. No.: WO2008/053901
PCT Pub. Date: May 8, 2008

(65) Prior Publication Data
US 2010/0248211 A1    Sep. 30, 2010

(30) Foreign Application Priority Data
Oct. 30, 2006 (JP) ................ 2006-294906
May 18, 2007 (JP) ................ 2007-133539

(51) Int. Cl.
*G01N 33/545* (2006.01)
*C12Q 1/70* (2006.01)
*G01N 33/576* (2006.01)
*C07K 16/08* (2006.01)

(52) U.S. Cl.
CPC .......... *G01N 33/5764* (2013.01); *C07K 16/082* (2013.01)

(58) Field of Classification Search
None
See application file for complete search history.

(56) References Cited

U.S. PATENT DOCUMENTS

| 4,599,231 A | 7/1986 | Milich et al. |
| 5,196,194 A * | 3/1993 | Rutter et al. ............... 424/189.1 |
| 7,393,933 B1 * | 7/2008 | Tedder et al. ............. 530/387.3 |
| 2008/0193916 A1 | 8/2008 | Maki et al. |

FOREIGN PATENT DOCUMENTS

| EP | 0 456 215 A1 | 11/1991 |
| EP | 1806363 A1 | 7/2007 |
| JP | 4-228087 A | 8/1992 |
| JP | 2003-83976 A | 3/2003 |
| WO | WO 98/29441 A1 | 7/1998 |
| WO | WO 2006/033368 A1 | 3/2006 |

OTHER PUBLICATIONS

Morris, Glenn. Epitope Mapping of Protein Antigens by Competition ELISA. The Protein Protocols Handbook. 1996, Part V, p. 595-600.*
Supplementary European Search Report for Application No. 07830884.8 dated Jun. 17, 2010.
Ijaz et al., "Novel Immunoassay for the Detection of Hepatitis B Surface 'Escape' Mutants and Its Application in Liver Transplant Recipients", Journal of Medical Virology, vol. 63 (2001) pp. 210-216.
Prange et al., "Novel Transmembrane Topology of the Hepatitis B Virus Envelope Proteins", The EMBO Journal; vol. 14, No. 2 (1995) pp. 247-256.

* cited by examiner

*Primary Examiner* — Michelle S Horning
(74) *Attorney, Agent, or Firm* — Birch, Stewart, Kolasch & Birch, LLP

(57) ABSTRACT

An object of the present invention is to enable to accurately quantify HBs antigen in the samples for which measured values are low or false-negative results by the conventional assaying method of HBs antigen. In the method of assaying HBs antigen according to the present invention, at least one inner capture probe that binds to a first inner region peptide consisting of 26th to 80th amino acid residues of HBs antigen and at least one outer capture probe that binds to a second outer region peptide consisting of 98th to 156th amino acid residues of HBs antigen are used as capture probes; and at least one inner detection probe which binds to the first inner region and at least one outer detection probe which binds to the second outer region are used as detection probes.

2 Claims, 1 Drawing Sheet

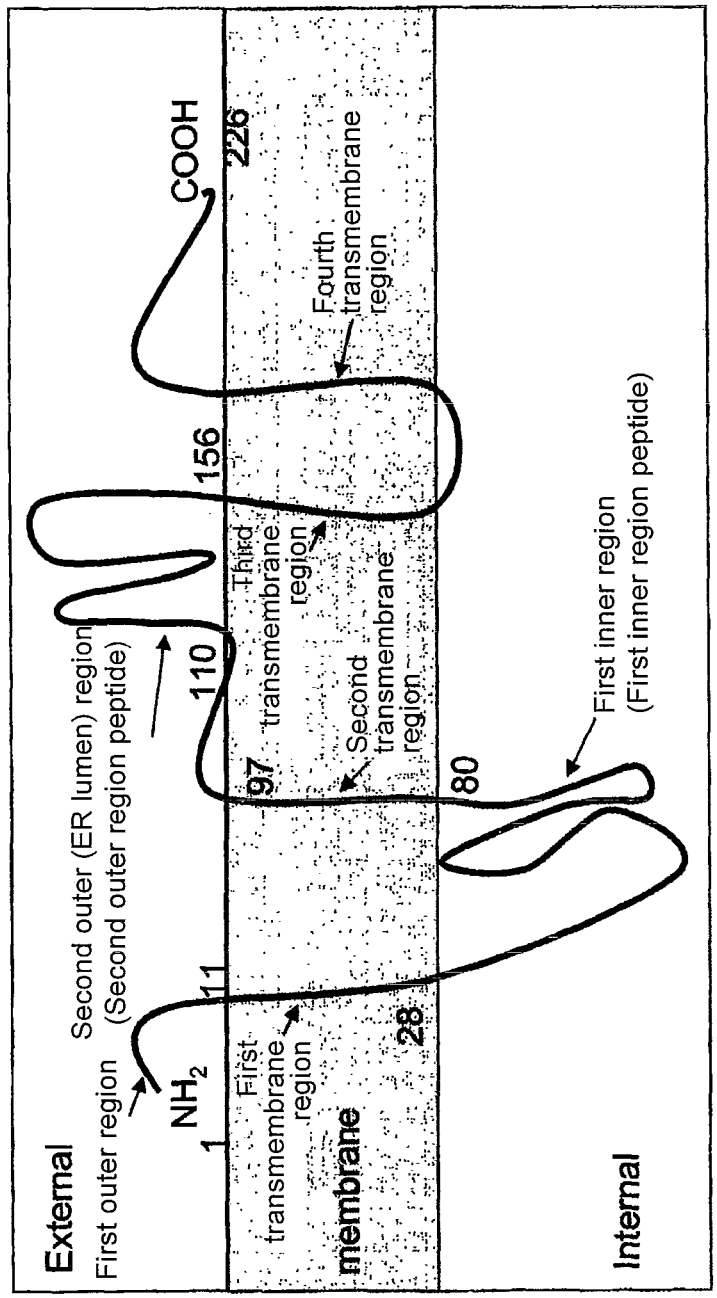

METHOD FOR ANALYSIS OF HEPATITIS B VIRUS S ANTIGEN

TECHNICAL FIELD

The present invention relates to a method for assaying hepatitis B virus surface antigen and a monoclonal antibody which binds to hepatitis B virus surface antigen. According to the present invention, hepatitis B virus surface antigen (this may be hereinafter referred to as HBs antigen) in a test sample (this may be hereinafter referred to as a sample) can be accurately assayed by measuring HBs antigen using a probe which binds to the first inner region peptide of HBs antigen and a probe which binds to the second outer region peptide of the antigen, which probes are especially monoclonal antibodies.

BACKGROUND ART

Blood used in transfusion often causes post-transfusion infection. Hepatitis B virus (this may be hereinafter referred to as HBV) is a causative virus of post-transfusion hepatitis, which infects through transfusion in surgery or the like. Therefore, it is extremely important to diagnose whether or not the blood is infected with HBV by screening of the blood for transfusion. As a method to diagnose such HBV infection, a method to assay HBs antigen, in which HBs antigen is detected and quantified, is widely used.

HBs antigen is a major structural envelope protein on the surface of an infectious HBV particle and contained in the lipid bilayer membrane derived from hepatic cells, which membrane wraps the core particle containing HBV-DNA. Blood of a patient infected with HBV also contains noninfectious small spherical particles and tubular particles which are without the core particle and composed of HBs antigen. The small spherical particles exist in the blood most abundantly and are observed at ratios of about 1000 small spherical particles relative to 1 to several HBV particles. Currently available diagnostic reagents for HBs antigen detect mainly HBs antigen in the form of the small spherical particle.

HBs antigen is a membrane protein having the total length of 226 amino acid residues, which penetrates the lipid bilayer membrane 4 times. Although the model for the transmembrane structure of HBs antigen has not been completely elucidated yet, Howard et al. proposed that HBs antigen is made of: the first outer region (ER lumen side) of the lipid bilayer membrane, consisting of 1st to 11th residues of the N-terminus of HBs antigen; the first transmembrane region consisting of 12th to 28th amino acid residues, which penetrates the lipid bilayer membrane and is hydrophobic; the first inner region of the lipid bilayer membrane, consisting of 29th to 80th residues; the second transmembrane region consisting of 81st to 97th amino acid residues, which is hydrophobic; the second outer (ER lumen) region consisting of 98th to 156th amino acid residues, which is hydrophilic; and the third transmembrane region, second inner region, fourth transmembrane region and third outer (ER lumen) region consisting of the 157th amino acid residue and residues more distant from the N-terminus (Non-patent Literature 1: FIG. 1).

As the conventional method for assaying HBs antigen, methods using an antibody which binds to the common antigenic determinant a of HBs antigen have been common. The common antigenic determinant a of HBs antigen is located on the peptide consisting of 110th to 156th amino acid residues in the second outer (ER lumen) region of HBs antigen, that is, 98th to 156th amino acid residues. The common antigenic determinant a has a complex high dimensional structure and, furthermore, it is reported to have four epitopes (Non-patent Literature 2).

On the other hand, the above method for assaying HBs antigen using an antibody which binds to the common antigenic determinant a is sometimes incapable of detecting HBV having an amino acid mutation(s) in the region of HBs antigen. Therefore, a method for assaying HBs antigen using an antibody which binds to the peptide in the first inner region of the lipid bilayer was recently developed, which peptide is consisting of 26th to 80th amino acid residues (Patent Literature 1).

Patent Literature 1 WO 2006/033368

Non-Patent Literature 1: Howard et al. "Viral Hepatitis and Liver Disease" (Zuckerman A J and Alan R (eds.)) (Liss Inc, New York) 1988, pp. 1094-1101

Non-Patent Literature 2: Hiroaki Okamoto "Nippon Rinsho, Molecular Hepatitis Virology, Fundamental-Clinic-Prophylaxis, Lower Volume, Hepatitis A, B, D, E Viruses", published on Oct. 26, 1995, pp. 212-222)

DISCLOSURE OF THE INVENTION

Problems to be Solved by the Invention

In a patient acutely infected with HBV, HBs antigen is positive in the initial phase of the infection and, subsequently, HBs antibody becomes positive and the HBs antigen turns negative. It was discovered that, when HBs antibody in the blood of a patient is positive and HBs antigen is assayed by a method using an antibody which binds to the common antigenic determinant a, the HBs antibody of the patient inhibits binding of the antibody used in the assaying method to the HBs antigen, so that the measured value decreases. Further, when HBs antigen was assayed by a method for assaying HBs antigen using an antibody which binds to the peptide in the first inner region of the lipid bilayer, which peptide is consisting of the 26th to 80th amino acid residues, it was discovered that there exists false-negative samples which cannot be assayed in spite of existence of the virus in the blood.

The present inventors intensively studied in an attempt to enable to accurately quantify HBs antigen in the samples for which measured values are low or false-negative results are obtained by the conventional assaying method of HBs antigen, and found an assaying method of HBs antigen in which antibodies recognizing peptides in specific regions of HBs antigen are used in combination, to eliminate occurrence of false negatives and to enable accurate quantification of HBs antigen.

The present invention is based on such a discovery.

MEANS FOR SOLVING THE PROBLEMS

Accordingly, the present invention relates to a method for assaying HBs antigen, characterized by using as capture probes at least one inner capture probe which binds to a first inner region peptide of HBs antigen and at least one outer capture probe which binds to a second outer region peptide of HBs antigen; and using as detection probes at least one inner detection probe which binds to the first inner region peptide and at least one outer detection probe which binds to the second outer region peptide.

In a preferred embodiment of the method for assaying HBs antigen according to the present invention, the epitope to which the inner capture probe binds and the epitope to which the inner detection probe binds are different, and the epitope to which the outer capture probe binds and the epitope to which the outer detection probe binds are different.

In another preferred embodiment of the method for assaying HBs antigen according to the present invention, the inner capture probe binds to a peptide consisting of 51st to 60th amino acids in the amino acid sequence shown in SEQ ID NO: 1; the outer capture probe binds to a peptide consisting of 111th to 130th amino acids in the amino acid sequence shown in SEQ ID NO: 1; the inner detection probe binds to a peptide consisting of 51st to 69th amino acids in the amino acid sequence shown in SEQ ID NO: 1; and the outer detection probe binds to a peptide consisting of 98th to 156th amino acids in the amino acid sequence shown in SEQ ID NO: 1.

In another preferred embodiment of the method for assaying HBs antigen according to the present invention, the probes are monoclonal antibodies or fragments thereof, and, in particular, the inner capture monoclonal antibody is selected from the group consisting of FERM BP-10117 antibody, FERM BP-10702 antibody, FERM BP-10700 antibody and FERM BP-10698 antibody; the inner detection monoclonal antibody is selected from the group consisting of FERM BP-10117 antibody, FERM BP-10702 antibody, FERM BP-10700 antibody and FERM BP-10698 antibody; the outer capture monoclonal antibody is selected from the group consisting of FERM BP-10699 antibody, FERM BP-10703 antibody, FERM BP-10701 antibody and FERM BP-10697 antibody; the outer detection monoclonal antibody is selected from the group consisting of FERM BP-10699 antibody, FERM BP-10703 antibody, FERM BP-10701 antibody and FERM BP-10697 antibody; the inner capture monoclonal antibody and the inner detection monoclonal antibody are different antibodies; and the outer capture monoclonal antibody and the outer detection monoclonal antibody are different antibodies.

The present invention also relates to a kit for assaying HBs antigen, which kit is characterized by comprising an antibodies-immobilized carrier comprising as capture probes at least one inner capture probe which binds to a first inner region peptide of HBs antigen and at least one outer capture probe which binds to a second outer region peptide of HBs antigen; and a reagent comprising as detection probes at least one inner detection probe which binds to the first inner region peptide and at least one outer detection probe which binds to the second outer region peptide.

The present invention further relates to a mouse hybridoma deposited under the international accession No. FERM BP-10702, FERM BP-10698, FERM BP-10699, FERM BP-10703, FERM BP-10701, FERM BP-10700 or FERM BP-10697.

The present invention further relates to a mouse hybridoma deposited under the international accession No. FERM BP-10702, FERM BP-10698, FERM BP-10699, FERM BP-10703, FERM BP-10701, FERM BP-10700 or FERM BP-10697, and a monoclonal antibody produced therefrom.

The present invention further relates to a method for assaying HBs antigen, which method comprises: (i) the contacting step wherein: at least one inner capture probe which binds to a first inner region peptide of HBs antigen and at least one outer capture probe which binds to a second outer region peptide of HBs antigen; a test sample; and at least one inner detection probe which binds to the first inner region peptide and at least one outer detection probe which binds to the second outer region peptide; are brought into contact; and (ii) the detection step wherein signals of the detection probes are detected.

As used herein, an "assay" includes both "detection" to judge the presence or absence of a compound to be assayed and "quantification" to determine abundance of a compound to be assayed.

The "method for assaying HBs antigen" according to the present invention can be used as a "diagnostic method for HBV".

EFFECT OF THE INVENTION

According to the present invention, it is possible to assay HBs antigen in the samples for which false-negative results are obtained by the conventional assaying method of HBs antigen. It is also possible to accurately quantify HBs antigen in the samples for which measured values are low in the conventional assaying method of HBs antigen.

BRIEF DESCRIPTION OF THE DRAWING

FIG. 1 is a schematic view of a transmembrane model of HBs antigen.

BEST MODE FOR CARRYING OUT THE INVENTION

The method of the present invention for assaying HBs antigen uses as capture probes at least one inner capture probe which binds to a first inner region peptide of HBs antigen and at least one outer capture probe which binds to a second outer region peptide of HBs antigen; and uses as detection probes at least one inner detection probe which binds to the first inner region peptide and at least one outer detection probe which binds to the second outer region peptide.

The HBs antigen measured by the method of the present invention for assaying HBs antigen is a membrane protein having the total length of 226 amino acid residues, which penetrates the lipid bilayer membrane 4 times. Several genotypes such as the genotypes A, B, C, D, E, F, and G are known in HBV, and the amino acid sequence of HBs antigen varies depending on the genotype. Genetic variations which vary among different virus strains are known, and many such variations are known especially in the outer 110th to 156th amino acids region of the lipid bilayer membrane of an HBV particle. HBs antigens having such amino acid sequences showing heterogeneity may be included in the HBs antigens to be measured by the assaying method of the present invention for assaying HBs antigen, and can be measured by the assaying method of the present invention.

FIG. 1 shows the transmembrane structure model of HBs antigen proposed by Howard et al. The first inner region peptide corresponds to, for example, the first inner region of the lipid bilayer consisting of 29th to 80th amino acid residues in the transmembrane structure model of HBs antigen proposed by Howard et al., but the peptide is not restricted to the amino acid Nos. 29th to 80th of HBs antigen and the amino acid Nos. may vary due to mutation, deletion and/or insertion of an amino acid(s) of HBs antigen. The second outer region peptide corresponds to, for example, the second outer (ER lumen) region which is hydrophilic and consisting of 98th to 156th amino acid residues in the transmembrane structure model of HBs antigen, but the peptide is not restricted to the amino acid Nos. 98th to 156th of HBs antigen and the amino acid Nos. may vary due to mutation, deletion and/or insertion of an amino acid(s) of HBs antigen.

The first inner region peptide is preferably a hydrophilic peptide consisting of 26th to 80th amino acid residues of HBs antigen, which peptide exists in the inner side of the lipid bilayer membrane of an HBV particle. It typically has the amino acid sequence corresponding to 26th to 80th amino acids in SEQ ID NO:1. However, the first inner region peptide in the present specification is not restricted to the peptide having the amino acid sequence corresponding to 26th to 80th amino acids in SEQ ID NO:1 of HBs antigen as long as it is the first peptide from the N-terminus of HBs antigen among those existing in the inner side of the lipid bilayer. Examples thereof may include, for example, peptides having amino acid sequences corresponding to different amino acid Nos. from the N-terminus and peptides having amino acid sequences which are the same as that corresponding to 26th to 80th amino acids in SEQ ID NO:1 except that 1 or more amino acids are substituted (mutated) at, deleted from, and/or inserted to 1 or more sites therein.

The second outer region peptide is preferably a hydrophilic peptide which exists in the ER lumen in the outer side of the lipid bilayer membrane of an HBV particle, which peptide is consisting of 98th to 156th amino acid residues of HBs antigen. It typically has the amino acid sequence corresponding to 98th to 156th amino acids in SEQ ID NO:1. However, the second outer region peptide in the present specification is not restricted to the peptide having the amino acid sequence corresponding to 98th to 156th amino acids in SEQ ID NO:1 of HBs antigen as long as it is the second peptide from the N-terminus of HBs antigen among those existing in the outer side (lumen side) of the lipid bilayer. Examples thereof may include, for example, peptides having amino acid sequences corresponding to different amino acid Nos. from the N-terminus and peptides having amino acid sequences which are the same as that corresponding to 98th to 156th amino acids in SEQ ID NO:1 except that 1 or more amino acids are substituted (mutated) at, deleted from, and/or inserted to 1 or more sites therein.

The inner capture probes and inner detection probes which may be used in the present invention are not restricted as long as they are capable of recognizing and binding to the first inner region peptide, and may include, for example, probes which bind to the peptide consisting of 26th to 80th amino acids in SEQ ID NO:1 and probes which bind to a peptide having an amino acid sequence which is the same as the one corresponding to 26th to 80th amino acids in SEQ ID NO:1 except that 1 or more amino acids are substituted (mutated) at, deleted from, and/or inserted to 1 or more sites therein. More particularly, probes are included, which probes bind to the peptide consisting of 31st to 50th amino acids, the peptide consisting of 51st to 60th amino acids, the peptide consisting of 51st to 69th amino acids, the peptide consisting of 51st to 70th amino acids, the peptide consisting of 21st to 40th amino acids, the peptide consisting of 71st to 90th amino acids and the peptide consisting of 61st to 80th amino acids in the amino acid sequence shown in SEQ ID NO:1; or to peptides having the same amino acid sequences as these except that their amino acids are partially substituted.

The outer capture probes and outer detection probes which may be used in the present invention are not restricted as long as they are capable of recognizing and binding to a second outer region peptide, and may include, for example, probes which bind to the peptide consisting of 98th to 156th amino acids in SEQ ID NO:1 and probes which bind to a peptide having an amino acid sequence which is the same as the one corresponding to 98th to 156th amino acids in SEQ ID NO:1 except that 1 or more amino acids are substituted (mutated) at, deleted from, and/or inserted to 1 or more sites therein. More particularly, the probes include those which bind to the peptide consisting of 121st to 130th amino acids, the peptide consisting of 151st to 170th amino acids, the peptide consisting of 111th to 130th amino acids, the peptide consisting of 121st to 140th amino acids, the peptide consisting of 98th to 156th amino acids in the amino acid sequence shown in SEQ ID NO:1; or to peptides having the same amino acid sequences as these except that their amino acids are partially substituted, respectively. Examples of the epitopes to which the outer capture probes bind further include a structural epitope having a complex high dimensional structure, such as the common antigenic determinant a. Therefore, there are also epitopes which may not be formed by a partial peptide consisting of only 98th to 156th amino acids in SEQ ID NO:1 but which may be formed by a peptide longer than this portion, for example, the total length peptide consisting of the 226 amino acid residues corresponding to the total length of HBs antigen. Examples of the outer capture probes and outer detection probes which may be used in the present invention include, for example, those capable of binding to a structural epitope which is formed by a peptide longer than a partial peptide consisting of only 98th to 156th amino acids in the amino acid sequence shown in SEQ ID NO:1 but which exists in the region consisting of 98th to 156th amino acids (this will be hereinafter referred to as a "region structural epitope in the second outer region").

The probes which may be used in the present invention are not restricted as long as they are molecules capable of binding to a first inner region peptide, second outer region peptide or region structural epitope in the second outer region. Examples thereof include polyclonal antibodies, monoclonal antibodies, recombinant antibodies, receptors and analogues. Monoclonal antibodies and fragments thereof are preferred.

The antibody fragments of the monoclonal antibodies are not restricted as long as these comprise an antigen binding region which binds to a first inner region peptide, outer region peptide or region structural epitope in the second outer region, and examples thereof include Fab, Fab', $F(ab')_2$ and Fv. These antibody fragments may be obtained by, for example, digesting the monoclonal antibody of the present invention by a conventional method using a proteolytic enzyme (such as pepsin or papain), and subsequently purifying the digested product by a conventional method for separation and purification of proteins.

Embodiments using antibodies, especially monoclonal antibodies as the probes are illustrated hereinbelow, but the method of the present invention for assaying HBs antigen may be similarly carried out also by using other probes.

The measurement principle of the method for assaying HBs antigen is not restricted as long as it is a method for detecting HBs antigen using a capture antibody/antibodies and detection antibody/antibodies, and is preferably sandwich assay. Examples of sandwich assay include the forward sandwich assay and reverse sandwich assay which are 2-step methods, as well as 1-step method.

The method for assaying HBs antigen may comprise (i) the contacting step wherein: at least one inner capture antibody which binds to a first inner region peptide of HBs antigen and at least one outer capture antibody which binds to a second outer region peptide of HBs antigen; a test sample; and at least one inner detection antibody which binds to the first inner region peptide and at least one outer detection antibody which binds to the second outer region peptide; are brought into contact; and (ii) the detection step wherein signals of the detection antibodies are detected.

The above contacting step may be carried out in two separate steps, that is, the first contacting step wherein at least one inner capture antibody which binds to a first inner region peptide of HBs antigen and at least one outer capture antibody which binds to a second outer region peptide of HBs antigen are brought into contact with a test sample; and the second contacting step wherein the antigen-antibody complex formed in the first contacting step is brought into contact with at least one inner detection antibody which binds to the first inner region peptide and at least one outer detection antibody which binds to the second outer region peptide.

More particularly, the forward sandwich assay may be carried out as follows. First, capture antibodies which bind to HBs antigen are immobilized on an insoluble carrier(s) such as a microplate or beads. Blocking is then carried out using an appropriate blocking agent (such as bovine serum albumin or gelatin) to prevent non-specific adsorption to the capture antibodies and insoluble carrier(s). To the plate or beads on which the capture antibodies were immobilized, a test sample containing HBs antigen is added together with the primary reaction solution, and the capture antibodies are brought into contact with and bound to the HBs antigen (the primary reaction step). Thereafter, the antigen unbound to the capture antibodies, and impurities, are washed away with an appropriate washing solution (for example, phosphate buffer containing a surfactant). Subsequently, labeled antibodies which recognize the captured HBs antigen and to which an enzyme such as horseradish peroxidase (HRP) is bound, are added thereto, to allow the labeled antibodies to bind to the captured antigen (the secondary reaction step). By this reaction, an immune complex of the capture antibodies—antigen—labeled antibodies is formed on the carriers) such as the microplate. After washing the unbound labeled antibodies away with the washing solution, a coloring substrate or luminescent substrate for the enzyme of the labeled antibodies is added, and the enzyme is allowed to react with the substrate, to allow detection of a signal.

The capture antibodies used in the method of the present invention for assaying HBs antigen are antibodies which capture HBs antigen in a test sample and, in the sandwich assay using the above insoluble carrier(s), these are immobilized antibodies immobilized on the insoluble carrier(s). At least one inner capture antibody which binds to a first inner region peptide of HBs antigen and at least one outer capture antibody which binds to a second outer region peptide of HBs antigen are used in combination as the capture antibodies. Besides these 2 antibodies, other antibodies may be further added and used as capture antibodies.

The detection antibodies used in the method of the present invention for assaying HBs antigen are antibodies which detect HBs antigen captured by the capture antibodies in a test sample, and in the sandwich assay using the above insoluble carrier(s), these are labeled antibodies labeled by an enzyme or the like. At least one inner detection antibody which binds to the first inner region peptide of HBs antigen and at least one outer detection antibody which binds to the second outer region peptide of HBs antigen are used in combination as the detection antibodies. Besides these 2 antibodies, other antibodies may be further added and used as detection antibodies.

The inner capture antibody and inner detection antibody which bind to the first inner region peptide of the HBs antigen preferably bind to different epitopes. "Different epitopes" means that the epitopes are not completely the same. For example, the epitopes of the two antibodies are completely the same in cases where these two antibodies are the same monoclonal antibodies or where the two antibodies are completely inhibited in the epitope inhibition test. Even in cases where the epitope of the inner capture antibody and the epitope of the inner detection antibody are partially overlapping, they may be used in the method of the present invention for assaying HBs antigen in many cases.

The outer capture antibody and outer detection antibody which bind to the second outer region peptide consisting of 98th to 156th amino acid residues of HBs antigen also preferably bind to different epitopes. "Different epitopes" means that the epitopes are not completely the same. For example, the epitopes of the two antibodies are completely the same in cases where these two antibodies are the same monoclonal antibodies or where the two antibodies are completely inhibited in the epitope inhibition test. Even in cases where the epitope of the outer capture antibody and the epitope of the outer detection antibody are partially overlapping, they may be used in the method of the present invention for assaying HBs antigen in many cases.

Examples of the epitopes which are recognized by the probes, in particular monoclonal antibodies or antibody fragments thereof, of the present invention include continuous epitopes composed of continuous amino acid residues and structural epitopes (discontinuous epitopes) which are formed by a sheet structure(s) and helix structure(s) of HBs antigen and composed of a combination of discontinuous amino acids.

Examples of the enzyme which labels the antibodies include horseradish peroxidase (HRP), alkaline phosphatase, β-galactosidase, luciferase and the like. Other than enzymes, luminescent substances such as acridinium derivatives, fluorescent substances such as europium, radioactive substances such as $I^{125}$ and the like may be used as labeling substances. The substrate and luminescence-inducing substance may be selected appropriately depending on the labeling substance.

Examples of the labeled antibodies in the present invention also include antibodies having, as detection markers, substances bound thereto such as haptens, low molecular weight peptides and lectins which may be used for detection of a signal of the antigen-antibody reaction. Examples of the haptens include biotin, dinitrophenyl (DNP), and FITC. For example, in cases where biotin is bound to the antibody to provide a probe complex, avidin, which has an affinity to biotin, may be labeled with an enzyme such as HRP, a fluorescent substance such as fluorescein or a luminescent substance such as an acridinium derivative; and the labeled avidin may be allowed to react with the probe complex, to allow detection of a signal by coloring, fluorescence, luminescence or the like.

The method for labeling of the antibody is not restricted and a conventional method may be used, and examples thereof include methods wherein the antibody is labeled directly with a label such as an enzyme, methods wherein the antibody and a label such as an enzyme are bound to a macromolecular compound such as dextran, and methods wherein a labeled antibody is bound to a macromolecular compound such as dextran.

Examples of the antibodies of the present invention include polyclonal antibodies from animals and monoclonal antibodies from human and mouse, and known methods may be used for immunizing the animals to obtain the antibodies and for obtaining hybridomas producing the monoclonal antibodies except that HBs antigen or a partial peptide of HBs antigen is used as an immunogen, which methods may be carried out according to, for example, those described in "Biochemistry Experiments Lecture, Continued Edition" (Japanese Biochemical Society ed.), or "Immunobiochemistry Research Techniques" (Japanese Biochemical Society ed). The HBs antigen used for the immunization may be virus particles or HBs antigen purified from virus particles. The HBs antigen, first inner region peptide and second outer region peptide may be obtained by, for example, expression of these antigens in *E. coli* by genetic recombination, and purification thereof. A partial peptide of HBs antigen may also be prepared by chemical synthesis by, for example, Fmoc solid phase synthesis or Boc solid phase synthesis. The synthesized peptide may be purified by a conventional method such as HPLC, and its terminal amino acid may be made to be cysteine whose SH group can be used to bind the peptide to a carrier protein, which bound peptide can then be used as an immunogen.

The antibodies of the present invention may be obtained by immunizing animals using the HBs antigen, first inner region peptide and second outer region peptide as immunogens. The animal to be immunized is not restricted, and examples thereof include sheep, goat, rabbit, mouse, rat, guinea pig, bird, bovine and equine. The HBs antigen, first inner region peptide and second outer region peptide are mixed and emulsified with an equal amount of Freund's complete adjuvant or Titer-Max gold (Titer Max), and the resulting mixture is administered to a rabbit subcutaneously or to a mouse intraperitoneally. Thereafter, the same immunomanipulation is repeated at intervals of 1 to 2 weeks. The antibodies of the present invention may be obtained by collecting blood from the animal immunized as above and obtaining serum or plasma therefrom.

The hybridoma of the present invention which produces the monoclonal antibody of the present invention may be obtained from the animal which was subjected to the above immunomanipulation. For example, after 2 weeks from subjecting a mouse to several times of the immunomanipulation, the HBs antigen, first inner region peptide and second outer region peptide dissolved in phosphate-buffered saline (PBS) are inoculated through the tail vein. Two to three days later, spleen containing lymphocytes which produce antibodies is aseptically removed from the mouse. These lymphocytes may be, for example, fused with myeloma cells to establish a hybridoma which produces a monoclonal antibody.

The cell fusion may be carried out, for example, by fusing lymphocytes and myeloma cells in the presence of polyethylene glycol. For example, known cells having markers such as hypoxanthine-guanine-phosphoribosyltransferase deficiency or thymidine kinase deficiency may be used as the myeloma cells. In particular, examples of the cells include p3·NS-1/1·Ag4.1 and SP2/0-Ag14. The fused cells are selected by killing unfused cells using a selection medium such as HAT medium.

Subsequently, presence or absence of antibody production in the culture supernatant of the grown hybridomas is screened. The screening may be carried out by measuring production of specific antibodies to the HBs antigen, first inner region peptide and second outer region peptide by using enzyme-linked immunosorbent assay (ELISA) or the like. The clonality of the monoclonal antibodies may be ensured by selecting clones of the hybridomas secreting antibodies of interest and further repeating subcloning by limiting dilution method. Thus, the hybridomas producing the antibodies of the present invention may be selected, and the hybridoma cell lines HBs121 [international accession No. FERM BP-10697], HBs123 [international accession No. FERM BP-10698], HBs136 [international accession No. FERM BP-10699], HBs163 [international accession No. FERM BP-10700], HBs605C3 [international accession No. FERM BP-10701], SF111 [international accession No. FERM BP-10702], SF124CS [international accession No. FERM BP-10703], which produce the monoclonal antibodies of the present invention, were deposited with International Patent Organism Depositary, National Institute of Advanced Industrial Science and Technology (address: AIST Tsukuba Central 6, 1-1-1 Higashi, Tsukuba, Ibaraki 305-8566, Japan) as of Oct. 12, 2006. The hybridoma cell line 6G6 [International Accession No. FERM BP-10117] has been deposited with International Patent Organism Depositary, National Institute of Advanced Industrial Science and Technology as of Sep. 9, 2004.

In the present specification, an antibody produced by a hybridoma cell line is designated by the name of the hybridoma cell line followed by the term "antibody", or by the name wherein the international accession number of the cell line is followed by the term "antibody". For example, the antibody produced by the hybridoma cell line HBs121 is referred to as "HBs121 antibody" or "FERM BP-10697 antibody".

The hybridomas of the present invention may be subcultured in an arbitrary known medium such as RPMI1640. The monoclonal antibody of the present invention may be prepared by culturing this hybridoma. For example, by adding 10% fetal bovine serum to RPMI1640 medium and culturing the hybridoma at 37° C. in the presence of 5% $CO_2$, the antibody is produced in the culture supernatant. Further, the antibody may be obtained by inoculating the hybridoma intraperitoneally to a mouse pretreated with pristane and recovering its ascites 10-20 days later, in which ascites the antibody was produced. The antibody of the present invention may be purified by a known method, for example, a purification method using ProteinG or ProteinA column, a method using an affinity column to which HBs antigen is bound, or a method using an ion-exchange column.

The epitope which is recognized by the obtained monoclonal antibody can be determined from the sequence of the HBs antigen, by enzyme-linked immunosorbent assay (ELISA) using a prepared recombinant antigen, first inner region peptide, second outer region peptide or chemically synthesized synthetic peptide with the length of 10 to 20 amino acids. The epitope of the monoclonal antibody produced by each hybridoma of the present invention was determined according to the reactivities with chemically-synthesized peptides having 20 amino acid residues which overlap with each other by 10 amino acid residues based on the amino acid sequences of HBs antigens having different genotypes. HBs121 antibody binds to the peptides consisting of 151st to 170th amino acid residues of the genotypes C and D, but does not bind to the peptides consisting of 151st to 170th amino acid residues of the genotypes A and B. HBs123 antibody binds to the peptides consisting of 31st to 50th amino acid residues of the genotypes A to D. HBs136 antibody binds to the peptides consisting of 111th to 130th amino acid residues of the genotypes A, C and D. HBs163 antibody binds to the peptides consisting of 31st to 50th amino acid residues of the genotypes A to D. SF111 antibody binds to the peptides consisting of 51st to 69th amino acid residues of the genotypes A, B and C. On the other hand, HBs605C3 antibody and SF124CS antibody did not bind to any of the peptides consisting of 20 amino acid residues. Since HBs605C3 antibody and SF124CS antibody bind to HBs antigen consisting of 1st to 226th amino acid residues, and bind to the peptide consisting of 98th to 156th amino acid residues, they are antibodies recognizing a structural epitope of HBs antigen, for example, the common antigenic determinant a. Further, 6G6 antibody used in the Examples below is an antibody which binds to the peptide consisting of 51st to 60th amino acid residues and, in particular, binds to the peptide consisting of 41st to 60th amino acid residues and the peptide consisting of 51st to 70th amino acid residues of HBs antigen.

The kit of the present invention for assaying HBs antigen by sandwich assay may comprise: an insoluble carrier (for example, a 96-well plate or beads) on which at least one inner capture probe that binds to a first inner region peptide of HBs antigen and at least one outer capture probe which binds to a second outer region peptide of HBs antigen are immobilized; and a reagent comprising as detection probes at least one inner detection probe which binds to the first inner region peptide and at least one outer detection probe which binds to the second outer region peptide. The reagent for assaying HBs antigen may be provided in the form of solution, and may also be provided in the form of freeze-dried powder. The kit of the present invention for assaying HBs antigen may comprise a hepatitis B virus antigen, other anti-hepatitis B virus antibody, a manufacturer's instruction and the like.

EXAMPLES

The present invention will now be described concretely by way of Examples and Comparative Examples below, although the scope of the present invention is not restricted by these.

Example 1

Establishment of Monoclonal Antibody-Producing Hybridoma (A) HBs Antigen

A DNA fragment encoding the peptide consisting of 26th to 80th amino acids of HBs antigen was incorporated into pATtrpE vector, which is an expression vector. The obtained pATtrpE-HBs(26-80) was expressed in *E. coli* HB101 strain, and the cells were collected. The expressed antigen was purified by gel filtration and ion-exchange columns to obtain TrpE-HBs(26-80) antigen. This TrpE-HBs(26-80) antigen, purchased rHBsAg (Yeast; Advanced Chemical) and rHBsAg (CHO; Anapure) were used for immunization, measurement of the antibody titer of the mouse by ELISA and screening by ELISA.

(B) Immunization

An antigen solution (2 mg/mL) of TrpE-HBs(26-80) antigen, rHBsAg (Yeast) or rHBsAg (CHO) was mixed and emulsified with an equal amount of Titer-Max Gold (Titer Max USA), and 0.1 mL of the resulting mixture was injected to the abdominal cavity or a footpad of female Balb/c mice of 4 to 6 weeks old, to immunize the mice (the first immunization). At 1-week intervals, 0.1 mL of a mixture prepared in the same manner was administered twice intraperitoneally (the second and third immunization). In some cases, the fourth or fifth immunization was additionally carried out. One week later, blood was collected from each mouse, and the antibody titer was measured according to the method (C) described later. With regard to the mice with increased antibody titers, an antigen solution (0.1 mg/mL) of TrpE-HBs(26-80) antigen, rHBsAg (Yeast) or rHBsAg (CHO) was diluted with an equal amount of PBS, and 0.1 mL of the dilution was administered to the mice intravenously (the final immunization). After three days from the final immunization, spleen or inguinal lymph node was removed aseptically and used for the cell fusion step (D) below.

(C) Measurement of Antibody Titer by ELISA

To a 96-well plate for ELISA (Nunc), 100 μL each of TrpE-HBs(26-80) antigen, rHBsAg (Yeast) antigen or rHBsAg (CHO) antigen (1 μg/mL) was placed and left to stand at 4° C. overnight. Each well of this plate was then blocked with phosphate buffered saline (PBS) containing 0.5% sodium caseinate and 2% sucrose for 30 minutes.

After removing the blocking solution, the serum obtained in the above step (B) was 1.000-fold to 1,000,000-fold diluted with PBS containing 0.1% sodium caseinate, 1% bovine serum albumin (BSA), 1 mM EDTA and 0.01% TWEEN 20, and 100 μl, of the resulting dilution was added to the well. The plate was left to stand at room temperature for 60 minutes and washed 3 times with 0.05% TWEEN 20/PBS (this will be hereinafter referred to as PBST). Subsequently, 100 μL of horseradish peroxidase (HRP)-labeled anti-mouse IgG antibody (goat, Jackson) (0.08 μg/mL) was added to the plate and left to stand at room temperature for 1 hour, followed by washing the plate 4 times with PBST again. To each well, 100 μL of OPD substrate solution [0.075M phosphate-citrate buffer (pH 5.0) containing 2.2 mM o-phenylenediamine and 0.03% aqueous hydrogen peroxide solution] was added, and the reaction was allowed to proceed at 25° C. for 30 minutes, followed by addition of 100 μL of 1M sulfuric acid. The absorbance at 492 nm of the sample in each well was measured.

(D) Cell Fusion

The spleen or inguinal lymph node removed aseptically was placed in a Petri dish containing 8 mL of RPMI1640 medium. After dissociating the spleen cells, these spleen or inguinal lymph node cells were passed through a mesh and collected in a 50 mL centrifugal tube. After adding 32 mL of RPMI1640 medium thereto, the resulting mixture was suspended and centrifuged at 150×g for 5 minutes. After aspirating the supernatant, the pellet was suspended in 40 mL of RPMI medium and centrifuged at 150×g for 5 minutes. This operation was carried out twice. The thus obtained cell pellet was resuspended in 40 mL of RPMI1640 medium, and spleen cells or lymph node cells were counted.

On the other hand, the spleen or lymph node cells (about $1 \times 10^8$ cells) were added to mouse myeloma cells SP2/0-Ag14 [RIKEN gene bank] (about $2 \times 10^7$ cells) precultured in a 50 mL tube, and the resulting mixture was mixed well in RPMI1640 medium, followed by centrifugation (150×g, 5 minutes). After aspirating the supernatant, the pellet was loosened well, and 1 mL of 50% polyethylene glycol (PEG) 4000 prewarmed to 37° C. was added dropwise thereto, followed by gently rotating the centrifugal tube by hand for 1 minute to mix the PEG solution and cell pellet. Subsequently, 9 mL of RPMI1640 medium prewarmed to 37° C. was added to the tube, which was then rotated gently. Centrifugation (150×g, 5 minutes) was then carried out and the supernatant was removed, followed by suspending the cell pellet in 50 mL of HAT medium (RPMI1640 medium containing aminopterin ($4 \times 10^{-7}$ M, final concentration), thymidine ($1.6 \times 10^{-5}$ M, final concentration), and hypoxanthine ($1 \times 10^{-4}$ M, final concentration)) containing 10% fetal bovine serum and 5% BriClone (human IL-6, Dainippon Pharmaceutical Co., Ltd.). This cell suspension was aliquoted in 100 μL volumes to wells of the 96-well cell culture plate, and culturing was started in a $CO_2$ incubator containing 5% carbon dioxide gas at 37° C. During the culturing, at 2 to 3 days' intervals, about 100 μL of the medium was removed from each well and 100 μL of the above HAT medium was freshly added thereto, to select hybridomas which proliferate in HAT medium. On around Day 10, screening of the following hybridomas was carried out.

(E) Screening of Hybridomas

Screening of hybridomas was carried out by repeating measurement of the antibody titer by ELISA in the same manner as in the above step (C) except that 100 μL of the culture supernatant of each hybridoma was used in place of the blood sample. Each of the hybridomas in the wells for which antibody production was observed was cloned by the limiting dilution method. ELISA was carried out similarly 10 days later to screen clones of hybridomas producing the monoclonal antibodies of the present invention. As a result, the hybridoma cell lines HBs121 [international accession No.

FERM BP-10697], HBs123 [international accession No. FERM BP-10698], HBs136 [international accession No. FERM BP-10699], HBs163 [international accession No. FERM BP-10700], HBs605C3 [international accession No. FERM BP-10701], SF111 [international accession No. FERM BP-10702] and SF124CS [international accession No. FERM BP-10703] were established. Each hybridoma was deposited with International Patent Organism Depositary, National Institute of Advanced Industrial Science and Technology (address: AIST Tsukuba Central 6, 1-1-1 Higashi, Tsukuba, Ibaraki 305-8566, Japan) as of Oct. 12, 2006.

The epitope of the monoclonal antibody produced by each hybridoma of the present invention was determined by ELISA using peptides having 20 amino acid residues derived from HBs antigen. Peptides having 20 amino acid residues or 19 amino acid residues which overlap with each other by 10 amino acid residues based on the amino acid sequences of HBs antigen having different genotypes were chemically synthesized and used as antigens for ELISA. The peptides used for determination of the epitopes are shown in Table 1. PepHBS1AD (SEQ ID NO:2), PepHBS1B (SEQ ID NO:3), PepHBS1C2 (SEQ ID NO:4) and PepHBS1C (SEQ ID NO:5) as peptides consisting of 1st to 20th amino acid residues; PepHBS2ACD (SEQ ID NO:6) and PepHBS2B (SEQ ID NO:7) as peptides consisting of 11th to 30th amino acid residues; PepHBS3ACD (SEQ ID NO:8) as a peptide consisting of 21st to 40th amino acid residues; PepHBS4A (SEQ ID NO:9), PepHBS4B (SEQ ID NO:10), PepHBS4C (SEQ ID NO:11) and PepHBS4D (SEQ ID NO:12) as peptides consisting of 31st to 50th amino acid residues; PepHBS5A (SEQ ID NO:13), PepHBS5B (SEQ ID NO:14), PepHBS5C (SEQ ID NO:15) and PepHBS5D (SEQ ID NO:16) as peptides consisting of 41st to 60th amino acid residues; PepHBS6AC (SEQ ID NO:17) and PepHBS6B (SEQ ID NO:18) as peptides consisting of 51st to 69th amino acid residues; PepHBS7AC (SEQ ID NO:19) and PepHBS7D (SEQ ID NO:20) as peptides consisting of 61st to 80th amino acid residues; PepHBS8ACD (SEQ ID NO:21) and PepHBS8B (SEQ ID NO:22) as peptides consisting of 71st to 90th amino acid residues; PepHBS9ACD (SEQ ID NO:23) as a peptide consisting of 81st to 100th amino acid residues; PepHBS10C (SEQ ID NO:24) as a peptide consisting of 91st to 110th amino acid residues; PepHBS11A (SEQ ID NO:25), PepHBS11BD (SEQ ID NO:26) and PepHBS11C (SEQ ID NO:27) as peptides consisting of 101st to 119th amino acid residues; PepHBS12A (SEQ ID NO:28), PepHBS12C (SEQ ID NO:29), PepHBS12D1 (SEQ ID NO:30) and PepHBS12D2 (SEQ ID NO:31) as peptides consisting of 111th to 130th amino acid residues; PepHBS13A (SEQ ID NO:32), PepHBS13B (SEQ ID NO:33), PepHBS13C (SEQ ID NO:34), PepHBS13D1 (SEQ ID NO:35) and PepHBS13D2 (SEQ ID NO:36) as peptides consisting of 121st to 140th amino acid residues; PepHBS14A (SEQ ID NO:37) and PepHBS14C (SEQ ID NO:38) as peptides consisting of 131st to 150th amino acid residues; PepHBS15C (SEQ ID NO:39) as a peptide consisting of 141st to 160th amino acid residues; PepHBS16AB (SEQ ID NO:40), PepHBS16C2 (SEQ ID NO:41), PepHBS16C (SEQ ID NO:42) and PepHBS16D (SEQ ID NO:43) as peptides consisting of 151st to 170th amino acid residues; PepHBS17C (SEQ ID NO:44) and PepHBS17D (SEQ ID NO:45) as peptides consisting of 161st to 180th amino acid residues; PepHBS18ABD (SEQ ID NO:46) and PepHBS18C (SEQ ID NO:47) as peptides consisting of 171st to 190th amino acid residues; PepHBS19A (SEQ ID NO:48) and PepHBS19C (SEQ ID NO:49) as peptides consisting of 181st to 200th amino acid residues; PepHBS20A (SEQ ID NO:50), PepHBS20B (SEQ ID NO:51) and PepHBS20C (SEQ ID NO:52) as peptides consisting of 191st to 210th amino acid residues; PepHBS21A (SEQ ID NO:53), PepHBS21B (SEQ ID NO:54), PepHBS21C (SEQ ID NO:55) and PepHBS21D (SEQ ID NO:56) as peptides consisting of 201st to 220th amino acid residues; and PepHBS22CD (SEQ ID NO:57) as a peptide consisting of 211th to 226th amino acid residues of HBs antigen were used. The character A, B, C, D or the like in the end of the name of each peptide indicates that the amino acid sequence of the peptide is an amino acid sequence of a representative genotype. Further, "AB" indicates that the amino acid sequence of the peptide is the common amino acid sequence between the genotypes A and B.

As the results of the epitope analysis, HBs121 antibody bound to PepHBS16C2, PepHBS16C and PepHBS16D which are peptides consisting of 151st to 170th amino acid residues, but did not bind to PepHBS16AB. HBs123 antibody bound to PepHBS4A, PepHBS4B and PepHBS4C which are peptides consisting of 31st to 50th amino acid residues, but did not bind to PepHBS4D. HBs136 antibody bound to PepHBS12A, PepHBS12C, PepHBS12D1 and PepHBS12D2 which are peptides consisting of 111th to 130th amino acid residues. HBs163 antibody bound to PepHBS4A, PepHBS4B and PepHBS4C which are peptides consisting of 31st to 50th amino acid residues, but did not bind to PepHBS4D. SF111 antibody bound to PepHBS6AC which is a peptide consisting of 51st to 69th amino acid residues, but did not bind to PepHBS6B. On the other hand, HBs605C3 antibody and SF124CS antibody bound to HBs antigen consisting of 1st to 226th amino acid residues, but did not bind to peptides having 20 amino acid residues.

TABLE 1

| No. | 1 | | | | 5 | | | | | 10 | | | | | 15 | | | | | 20 |
|---|---|---|---|---|---|---|---|---|---|---|---|---|---|---|---|---|---|---|---|---|
| PepHBS1AD | M | E | N | I | T | S | G | F | L | G | P | L | L | V | L | Q | A | G | F | F |
| PepHBS1B | M | E | N | I | A | S | G | L | L | G | P | L | L | V | L | Q | A | G | F | F |
| PepHBS1C2 | M | E | N | T | T | S | G | F | L | G | P | L | L | V | L | Q | A | G | F | F |
| PepHBS1C | M | E | S | T | T | S | G | F | L | G | P | L | L | V | L | Q | A | G | F | F |
| PepHBS2ACD | P | L | L | V | L | Q | A | G | F | F | L | L | T | R | I | L | T | I | P | Q |
| PepHBS2B | P | L | L | V | L | Q | A | G | F | F | L | L | T | K | I | L | T | I | P | Q |
| PepHBS3ACD | L | L | T | R | I | L | T | I | P | Q | S | L | D | S | W | W | T | S | L | N |
| PepHBS4A | S | L | D | S | W | W | T | S | L | N | F | L | G | G | S | P | V | C | L | G |
| PepHBS4B | S | L | D | S | W | W | T | S | L | N | F | L | G | G | T | P | V | C | L | G |
| PepHBS4C | S | L | D | S | W | W | T | S | L | N | F | L | G | G | A | P | T | C | P | G |
| PepHBS4D | S | L | D | S | W | W | T | S | L | N | F | L | G | G | T | T | V | C | L | G |

TABLE 1-continued

| No. | 1 | | | 5 | | | | | 10 | | | | | 15 | | | | | 20 |
|---|---|---|---|---|---|---|---|---|---|---|---|---|---|---|---|---|---|---|---|
| PepHBS5A | F | L | G | G | S | P | V | C | L | G | Q | N | S | Q | S | P | T | S | N | H |
| PepHBS5B | F | L | G | G | T | P | V | C | L | G | Q | N | S | Q | S | Q | I | S | S | H |
| PepHBS5C | F | L | G | G | A | P | T | C | P | G | Q | N | S | Q | S | P | T | S | N | H |
| PepHBS5D | F | L | G | G | T | T | V | C | L | G | Q | N | S | Q | S | P | T | S | N | H |
| PepHBS6AC | Q | N | S | Q | S | P | T | S | N | H | S | P | T | S | C | P | P | I | C | |
| PepHBS6B | Q | N | S | Q | S | Q | I | S | S | H | S | P | T | C | C | P | P | I | C | |
| PepHBS7AC | S | P | T | S | C | P | P | I | C | P | G | Y | R | W | M | C | L | R | R | F |
| PepHBS7D | S | P | T | S | C | P | P | T | C | P | G | Y | R | W | M | C | L | R | R | F |
| PepHBS8ACD | G | Y | R | W | M | C | L | R | R | F | I | I | F | L | F | I | L | L | L | C |
| PepHBS8B | G | Y | R | W | M | C | L | R | R | F | I | I | F | L | C | I | L | L | L | C |
| PepHBS9ACD | I | I | F | L | F | I | L | L | L | C | L | I | F | L | I | V | L | L | D | Y |
| PepHBS10C | L | I | F | L | L | V | L | L | D | Y | Q | G | M | L | P | V | C | P | L | L |
| PepHBS11A | Q | G | M | L | P | V | C | P | L | I | P | G | S | T | T | T | S | T | G | |
| PepHBS11BD | Q | G | M | L | P | V | C | P | L | I | P | G | S | S | T | T | S | T | G | |
| PepHBS11C | Q | G | M | L | P | V | C | P | L | L | P | G | T | S | T | T | S | T | G | |
| PepHBS12A | P | G | S | T | T | T | S | T | G | P | C | K | T | C | T | T | P | A | Q | G |
| PepHBS12C | P | G | T | S | T | T | S | T | G | P | C | K | T | C | T | I | P | A | Q | G |
| PepHBS12D1 | P | G | S | S | T | T | S | T | G | P | C | R | T | C | T | T | P | A | Q | G |
| PepHBS12D2 | P | G | S | S | T | T | S | T | G | P | C | R | T | C | M | T | T | A | Q | G |
| PepHBS13A | C | K | T | C | T | T | P | A | Q | G | N | S | M | F | P | S | C | C | C | T |
| PepHBS13B | C | K | T | C | T | T | P | A | Q | G | T | S | M | F | P | S | C | C | C | T |
| PepHBS13C | C | K | T | C | T | I | P | A | Q | G | T | S | M | F | P | S | C | C | C | T |
| PepHBS13D1 | C | R | T | C | T | T | P | A | Q | G | T | S | M | Y | P | S | C | C | C | T |
| PepHBS13D2 | C | R | T | C | M | T | T | A | Q | G | T | S | M | Y | P | S | C | C | C | T |
| PepHBS14A | N | S | M | F | P | S | C | C | C | T | K | P | T | D | G | N | C | T | C | I |
| PepHBS14C | T | S | M | F | P | S | C | C | C | T | K | P | S | D | G | N | C | T | C | I |
| PepHBS15C | K | P | S | D | G | N | C | T | C | I | P | I | P | S | S | W | A | F | A | R |
| PepHBS16AB | P | I | P | S | S | W | A | F | A | K | Y | L | W | E | W | A | S | V | R | F |
| PepHBS16C2 | P | I | P | S | S | W | A | F | A | K | F | L | W | E | W | A | S | V | R | F |
| PepHBS16C | P | I | P | S | S | W | A | F | A | R | F | L | W | E | W | A | S | V | R | F |
| PepHBS16D | P | I | P | S | S | W | A | F | G | K | F | L | W | E | W | A | S | A | R | F |
| PepHBS17C | F | L | W | E | W | A | S | V | R | F | S | W | L | S | L | L | V | P | F | V |
| PepHBS17D | F | L | W | E | W | A | S | A | R | F | S | W | L | S | L | L | V | P | F | V |
| PepHBS18ABD | S | W | L | S | L | L | V | P | F | V | Q | W | F | V | G | L | S | P | T | V |
| PepHBS18C | S | W | L | S | L | L | V | P | F | V | Q | W | F | A | G | L | S | P | T | V |
| PepHBS19A | Q | W | F | V | G | L | S | P | T | V | W | L | S | A | I | W | M | M | W | Y |
| PepHBS19C | Q | W | F | A | G | L | S | P | T | V | W | L | S | V | I | W | M | M | M | Y |
| PepHBS20A | W | L | S | A | I | W | M | M | W | Y | W | G | P | S | L | Y | S | I | V | S |
| PepHBS20B | W | L | S | V | I | W | M | M | W | F | W | G | P | S | L | Y | N | I | L | S |
| PepHBS20C | W | L | S | V | I | W | M | M | W | Y | W | G | P | S | L | Y | N | I | L | S |
| PepHBS21A | W | G | P | S | L | Y | S | I | V | S | P | F | I | P | L | L | P | I | F | F |
| PepHBS21B | W | G | P | S | L | Y | N | I | L | S | P | F | M | P | L | L | P | I | F | F |
| PepHBS21C | W | G | P | S | L | Y | N | I | L | S | P | F | L | P | L | L | P | I | F | F |
| PepHBS21D | W | G | P | S | L | Y | S | I | L | S | P | F | L | P | L | L | P | I | F | F |
| PepHBS22CD | P | F | L | P | L | L | P | I | F | F | C | L | W | V | Y | I | | | | |

Example 2

Preparation of Established Monoclonal Antibody (A) Preparation of Monoclonal Antibody from Culture Supernatant Each of the established hybridoma was cultured in a serum-free medium (Hybridoma-SFM, GIBCO) at 37° C. under 5% carbon dioxide atmosphere for 72 to 96 hours. The culture medium was applied to a recombinant protein A column (GE Healthcare Bio-Science KK). The antibody was eluted from the column using a buffer at pH5.5 to obtain the purified monoclonal antibody of the present invention. About 10 mg of the antibody was obtained from 500 mL of the culture medium.

(B) Preparation of Monoclonal Antibody from Ascites

To Balb/c mice of 4 to 6 weeks old, 0.5 mL per mouse of pristane was intraperitoneally administered, and, 7 days later, each of the proliferated hybridomas was intraperitoneally inoculated so as to achieve the cell number of $5 \times 10^6$ per mouse. About 15 mL of ascites was obtained from 5 individuals of mice, and about 10 mg of an antibody was obtained from 2 mL of the ascites. Purification of the monoclonal antibody in the ascites was carried out in the same manner as in the above described process for purification thereof from the culture supernatant.

Example 3

HRP Labeling of Monoclonal Antibody

HRP labeling of the antibody was carried out using EZ-Link Plus Activated Peroxidase from Pierce. This method binds HRP, to which an aldehyde group was introduced, to an amino group in the antibody molecule. Labeling was carried out according to the protocol provided by the manufacturer.

Example 4

In this Example 4, HBs antigen in the sample of an HBV-infected patient was measured using as the capture antibody/antibodies for sandwich assay the sole inner capture antibody, the sole outer capture antibody, or the combination of the inner capture antibody and outer capture antibody, and using as the detection antibody/antibodies the sole inner detection antibody, the sole outer detection antibody, or the combination of the inner detection antibody and outer detection antibody.

The 6G6 antibody as the inner capture antibody, HBs136 antibody as the outer capture antibody, SF111 antibody as the inner detection antibody, and SF124CS antibody as the outer detection antibody were used. At a concentration of 4 µg/mL, 100 µL of the sole 6G6 antibody, sole HBs136 antibody, or the mixed antibody wherein equal amounts of 6G6 antibody and HBs136 antibody were mixed was added to each well of a 96-well microplate (Costar 2592), and incubated at 4° C. overnight. After washing the plate twice with 10 mM phosphate buffer, pH 7.3, containing 0.15 M NaCl, 350 µL of 10 mM phosphate buffer containing 0.5% sodium caseinate was added to each well, and blocking was carried out at 37° C. for 5 hours. After removal of the blocking solution, 25 µL of reaction buffer (pH 7.2) containing 2% sodium N-lauroyl-sarcosinate (NLS) (WAKO) and 75 µL of a normal individual sample or HBV-positive sample were added to each well, and the reaction was allowed to proceed with stirring at room temperature for 1 hour.

This reaction was followed by 8 times of washing with 10 mM phosphate buffer, pH 7.3, containing 0.05% TWEEN 20 (washing solution). Subsequently, horseradish peroxidase-labeled SF124CS antibody, SF111 antibody, or the mixed antibody wherein equal amounts of SF124CS antibody and SF111 antibody were mixed was diluted with 10 mM phosphate buffer, pH 7.3, containing 2% BSA, 1% mouse serum and 0.2% Triton X-100, and 100 µL of the dilution was added to each well to allow the reaction to proceed with stirring at room temperature for 1 hour. After 8 times of washing with the washing solution, 100 µL of a substrate solution (o-phenylenediamine, SIGMA) was added to each well, and the resulting mixture was incubated at room temperature for 30 minutes until the reaction was stopped by adding 100 µL of 2N sulfuric acid to each well. The absorbance (O.D.) at 492 nm was measured by a detector from TOSOH using the absorbance at 620 nm as the control. The results are shown in Table 2. The results from the normal sample were indicated as O.D., and the results from the HBV-positive samples were indicated as Signal/Negative (S/N) which was calculated by dividing the O.D. of the HBV-positive sample by the O.D. of the normal sample. When S/N was not more than 1, the result was regarded as N.D. (Nondetectable). In Table 2, Int represents 6G6 antibody and Ext represents HBs136 antibody which are the capture antibodies, and Int represents SF111 antibody and Ext represents SF124CS antibody which are the detection antibodies.

When Int was solely used as the capture antibody in the method for assaying HBs antigen, HBs antigen in the HBV-positive samples 4, 5 and 6 could not be measured. Further, when Int was solely used as the detection antibody in the method for assaying HBs antigen, HBs antigen in the HBV-positive samples 4, 5 and 6 could not be measured, and the measured values of HBs antigen in the HBV-positive samples 10 and 12 were extremely low. On the other hand, when Ext was used as the capture antibody and Ext was used as the detection antibody; when Ext was used as the capture antibody and Int+Ext was used as the detection antibody; when Int+Ext was used as the capture antibody and Ext was used as the detection antibody; or when Int+Ext was used as the capture antibody and Int+Ext was used as the detection antibody; all the HBs-positive samples were able to be measured.

TABLE 2

| | | Capture antibody/Detection antibody | | | | | | | | |
|---|---|---|---|---|---|---|---|---|---|---|
| Genotype | Sample ID | Int/Int | Int/Ext | Int/Int + Ext | Ext/Int | Ext/Ext | Ext/Int + Ext | Int + Ext/Int | Int + Ext/Ext | Int + Ext/Int + Ext |
| A | HBV-positive sample 1 | 14.0 | 40.9 | 30.2 | 16.9 | 14.3 | 23.8 | 14.8 | 21.2 | 18.0 |
| A | HBV-positive sample 2 | 19.2 | 58.6 | 43.3 | 13.6 | 14.0 | 20.7 | 14.7 | 29.3 | 23.5 |
| A | HBV-positive sample 3 | 8.6 | 18.4 | 15.5 | 9.9 | 8.3 | 13.6 | 8.5 | 10.0 | 10.2 |
| B | HBV-positive sample 4 | N.D. | N.D. | N.D. | N.D. | >125.0 | >73.2 | N.D. | 28.5 | 16.4 |
| B | HBV-positive sample 5 | N.D. | N.D. | N.D. | N.D. | 52.4 | 25.9 | N.D. | 13.5 | 7.1 |
| B | HBV-positive sample 6 | N.D. | N.D. | N.D. | N.D. | >125.0 | 53.3 | N.D. | 22.3 | 14.1 |
| C | HBV-positive sample 7 | 42.1 | >111.1 | >76.9 | 36.0 | 42.8 | 50.0 | 20.6 | 31.8 | 16.7 |
| C | HBV-positive sample 8 | 46.8 | >111.1 | >76.9 | 41.4 | 61.7 | 56.7 | 18.5 | 35.5 | 20.3 |
| C | HBV-positive sample 9 | 16.5 | 76.4 | 45.7 | 21.0 | 24.3 | 30.8 | 10.6 | 23.5 | 14.1 |
| D | HBV-positive sample 10 | 1.7 | >111.1 | 45.8 | 6.0 | 58.8 | 31.2 | 3.0 | 20.0 | 14.8 |
| D | HBV-positive sample 11 | >66.7 | >111.1 | 42.4 | >54.5 | 89.9 | >73.2 | 13.8 | 21.3 | 14.9 |
| D | HBV-positive sample 12 | N.D. | 34.8 | 20.6 | 1.8 | 8.0 | 6.6 | 1.4 | 13.4 | 8.5 |
| — | Normal sample O.D. | 0.045 | 0.027 | 0.039 | 0.055 | 0.024 | 0.041 | 0.058 | 0.044 | 0.050 |

Example 5

In this Example 5, HBs antigen was measured under the conditions of HBs antibody-negative and HBs antibody-positive in the method for assaying HBs antigen using combinations of the capture antibodies and detection antibodies, which combinations were employed in Example 4. More particularly, HBs antibody-positive plasma with a high antibody titer was added to HBs antigen-positive test samples, and the influences thereof were investigated.

The 6G6 antibody as the inner capture antibody, HBs136 antibody as the outer capture antibody, SF111 antibody as the inner detection antibody, and SF124CS antibody as the outer detection antibody were used. At a concentration of 4 μg/mL, 100 μL of a solution of the sole 6G6 antibody, sole HBs136 antibody, or the mixture of equal amounts of 6G6 antibody and HBs136 antibody was added to each well of a 96-well microplate (Costar 2592) and incubated at 4° C. overnight. After washing the plate twice with 10 mM phosphate buffer, pH 7.3, containing 0.15 M NaCl, 350 μL of 10 mM phosphate buffer containing 0.5% sodium caseinate was added to each well, and blocking was carried out at 37° C. for 5 hours. After removal of the blocking solution, 25 μL of reaction buffer (pH 7.2) containing 2% NLS (WAKO) and 75 μL of a normal sample or HBV-positive sample diluted with HBs antibody-negative or HBs antibody-positive plasma were added to each well, and the reaction was allowed to proceed with stirring at room temperature for 1 hour.

This reaction was followed by 5 times of washing with 10 mM phosphate buffer, pH 7.3, containing 0.05% TWEEN 20 (washing solution). Subsequently, horseradish peroxidase-labeled SF111 antibody, SF124CS antibody or the mixed antibody wherein equal amounts of these antibodies were mixed was diluted with 10 mM phosphate buffer, pH 7.3, containing 2% BSA, 1% mouse serum and 0.2% Triton X-100, and 100 μL of the dilution was added to each well to allow the reaction to proceed with stirring at room temperature for 1 hour. After 5 times of washing with the washing solution, 100 μL of a substrate solution (o-phenylenediamine, SIGMA) was added to each well, and the resulting mixture was incubated at room temperature for 30 minutes until the reaction was stopped by adding 100 μL of 2N sulfuric acid to each well. The absorbance (O.D.) at 492 nm was measured by a detector from TOSOH using the absorbance at 620 nm as the control. The results are shown in Table 3. The percentages of the values obtained from the samples diluted with the HBs antibody-positive plasma relative to the values (defined as 100%) obtained from the samples diluted with the HBs antibody-negative plasma were represented as inhibition (%). In Table 3, Int represents 6G6 antibody and Ext represents HBs136 antibody which are the capture antibodies (1st Ab), and Int represents SF111 antibody and Ext represents SF124CS antibody which are the detection antibodies (2nd Ab).

When EXt was solely used as the capture antibody in the method for assaying HBs antigen, all the measured values were not more than 63.5% in the HBV-positive samples 1 and 8, and not more than 44.2% in the HBV-positive sample 3. On the other hand, when Int or Int+Ext was used as the capture antibody in the method for assaying HBs antigen, all the measured values were not less than 72.3% in the HBV-positive samples 1 and 8, and not less than 59.4% in the HBV-positive sample 3. Thus, it was suggested that the method for assaying HBs antigen using Int or Int+Ext as the capture antibody was less likely to be affected by the anti-HBs antibody in the body of a patient.

TABLE 3

| | | HBV-positive sample 1 | | | HBV-positive sample 3 | | | HBV-positive sample 8 | | |
|---|---|---|---|---|---|---|---|---|---|---|
| 1st Ab | 2nd Ab | HBs Ab (−) | HBs Ab (+) | inhibition (%) | HBs Ab (−) | HBs Ab (+) | inhibition (%) | HBs Ab (−) | HBs Ab (+) | inhibition (%) |
| Int | Int | 0.355 | 0.346 | 97.4 | 0.123 | 0.088 | 69.6 | 1.034 | 1.094 | 105.8 |
| | Ext | 0.279 | 0.236 | 84.0 | 0.061 | 0.047 | 73.7 | 2.019 | 1.461 | 72.3 |
| | Int + Ext | 0.389 | 0.350 | 89.8 | 0.109 | 0.088 | 79.2 | 1.991 | 1.573 | 78.9 |
| Ext | Int | 0.316 | 0.199 | 62.2 | 0.135 | 0.061 | 41.8 | 0.404 | 0.256 | 62.8 |
| | Ext | 0.083 | 0.048 | 60.4 | 0.030 | 0.010 | 35.4 | 0.230 | 0.125 | 55.1 |
| | Int + Ext | 0.267 | 0.171 | 63.5 | 0.117 | 0.054 | 44.2 | 0.455 | 0.279 | 61.0 |
| Int + Ext | Int | 0.499 | 0.428 | 85.3 | 0.156 | 0.096 | 59.4 | 1.334 | 1.255 | 93.9 |
| | Ext | 0.264 | 0.194 | 73.6 | 0.052 | 0.035 | 67.6 | 1.556 | 1.230 | 79.1 |
| | Int + Ext | 0.497 | 0.409 | 81.9 | 0.146 | 0.095 | 63.4 | 1.815 | 1.619 | 89.1 |

The results in the above Table 2 and Table 3 are summarized in Table 4. In Table 2, the combinations of the antibodies with which all the samples could be measured are represented by ○. In Table 3, the combinations of the antibodies with which the measured values were not less than 80% in the HBV-positive sample 1, with which the measured values were not less than 60% in the HBV-positive sample 3, or with which the measured values were not less than 80% in the HBV-positive sample 8 in Example 5 are represented by ○.

TABLE 4

| | | | Table 3 | | |
|---|---|---|---|---|---|
| Capture antibody | Detection antibody | Table 2 | HBV-positive sample 1 | HBV-positive sample 3 | HBV-positive sample 8 |
| Int | Int | X | ○ | ○ | ○ |
| | Ext | X | ○ | ○ | X |
| | Int + Ext | X | ○ | ○ | X |
| Ext | Int | X | X | X | X |
| | Ext | ○ | X | X | X |
| | Int + Ext | ○ | X | X | X |
| Int + Ext | Int | X | ○ | X | ○ |
| | Ext | ○ | X | ○ | X |
| | Int + Ext | ○ | ○ | ○ | ○ |

As shown in Table 4, it was discovered that occurrence of false-negatives is decreased by using Int+Ext as the capture antibody and using Int+Ext as the detection antibody, so that development of a method for assaying HBs antigen which is less likely to be affected by the anti-HBs antibody in the body of a patient is possible.

Industrial Applicability

By using the method of the present invention for assaying HBs antigen in screening of HBV infection, it is possible to assay a test sample infected by HBV which could not be assayed by the conventional method. It is also possible to quantify HBs antigen in an HBV-infected patient more accurately to help grasping of the diseased state of the patient.

The present invention was illustrated hereinbefore referring to specific embodiments, but modifications and improvements which are obvious to those skilled in the art are within the scope of the present invention.

The invention claimed is:

1. A method for assaying hepatitis B virus surface (HBs) antigen of the amino acid sequence set forth in SEQ ID NO:1, comprising the following steps:
contacting at least one inner capture antibody or a fragment comprising an antigen binding region thereof which binds to a first inner region peptide of HBs antigen and at least one outer capture antibody or a fragment comprising an antigen binding region thereof which binds to a second outer region peptide of HBs antigen with a test sample, and at least one inner detection antibody or a fragment comprising an antigen binding region thereof which binds to said first inner region and at least one outer detection antibody or a fragment comprising an antigen binding region thereof which binds to said second outer region, and
detecting signals of the detection antibodies,
wherein the presence of detection signals indicate the presence of HBs antigen in the test sample,
wherein said antibodies or fragments comprising an antigen binding region thereof are monoclonal antibodies or antigen binding fragments thereof, and
wherein said inner capture monoclonal antibody is selected from the group consisting of FERM BP-10117 antibody, FERM BP-10702 antibody, FERM BP-10700 antibody and FERM BP-10698 antibody; said inner detection monoclonal antibody is selected from the group consisting of FERM BP-10117 antibody, FERM BP-10702 antibody, FERM BP-10700 antibody and FERM BP-10698 antibody; said outer capture monoclonal antibody is selected from the group consisting of FERM BP-10699 antibody, FERM BP-10703 antibody, FERM BP-10701 antibody and FERM BP-10697 antibody; said outer detection monoclonal antibody is selected from the group consisting of FERM BP-10699 antibody, FERM BP-10703 antibody, FERM BP-10701 antibody and FERM BP-10697 antibody; said inner capture monoclonal antibody and said inner detection monoclonal antibody are different antibodies; and said outer capture monoclonal antibody and said outer detection monoclonal antibody are different antibodies.

2. A method for assaying hepatitis B virus surface (HBs) antigen of the amino acid sequence set forth in SEQ ID NO:1, comprising the following steps:
contacting at least one inner capture antibody or a fragment comprising an antigen binding region thereof which binds to a first inner region peptide of HBs antigen and at least one outer capture antibody or a fragment comprising an antigen binding region thereof which binds to a second outer region peptide of HBs antigen with a test sample, and at least one inner detection antibody or a fragment comprising an antigen binding region thereof which binds to said first inner region and at least one outer detection antibody or a fragment comprising an antigen binding region thereof which binds to said second outer region, and
detecting signals of the detection antibodies,
wherein the presence of detection signals indicate the presence of HBs antigen in the test sample,
wherein the epitope to which said inner capture antibody or a fragment comprising an antigen binding region thereof binds and the epitope to which said inner detection antibody or a fragment comprising an antigen binding region thereof binds are different, and the epitope to which said outer capture antibody or a fragment comprising an antigen binding region thereof binds and the epitope to which said outer detection antibody or a fragment comprising an antigen binding region thereof binds are different, and wherein said inner capture antibody or a fragment comprising an antigen binding region thereof binds to a peptide consisting of 51st to 60th amino acids in the amino acid sequence shown in SEQ ID NO: 1; said outer capture antibody or a fragment comprising an antigen binding region thereof binds to a peptide consisting of 111th to 130th amino acids in the amino acid sequence shown in SEQ ID NO: 1; said inner detection antibody or a fragment comprising an antigen binding region thereof binds to a peptide consisting of 51st to 69th amino acids in the amino acid sequence shown in SEQ ID NO: 1; and said outer detection antibody or a fragment comprising an antigen binding region thereof binds to a peptide consisting of 98th to 156th amino acids in the amino acid sequence shown in SEQ ID NO: 1, and wherein said inner capture monoclonal antibody binds to the same epitope as a monoclonal antibody selected from the group consisting of FERM BP-10117 antibody, FERM BP-10702 antibody, FERM BP-10700 antibody and FERM BP-10698 antibody; said inner detection monoclonal antibody binds to the same epitope as a monoclonal antibody selected from the group consisting of FERM BP-10117 antibody, FERM BP-10702 antibody, FERM BP-10700 antibody and FERM BP-10698 antibody; said outer capture monoclonal antibody binds to the same epitope as a monoclonal antibody selected from the group consisting of FERM BP-10699 antibody, FERM BP-10703 antibody, FERM BP-10701 antibody and FERM BP -10697 antibody; said outer detection monoclonal antibody binds to the same epitope as a monoclonal antibody selected from the group consisting of FERM BP-10699 antibody, FERM BP-10703 antibody, FERM BP-10701 antibody and FERM BP-10697 antibody.

* * * * *

SEQUENCE LISTING

<160> NUMBER OF SEQ ID NOS: 57

<210> SEQ ID NO 1
<211> LENGTH: 226
<212> TYPE: PRT
<213> ORGANISM: Hepatitis B virus

<400> SEQUENCE: 1

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Ile Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
            115                 120                 125

Gln Gly Asn Ser Met Phe Pro Ser Cys Cys Thr Lys Pro Thr Asp
        130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
            195                 200                 205

Val Ser Pro Phe Leu Pro Leu Leu Pro Ile Phe Phe Cys Leu Trp Val
    210                 215                 220

Tyr Ile
225

<210> SEQ ID NO 2
<211> LENGTH: 20
<212> TYPE: PRT
<213> ORGANISM: Hepatitis B virus

<400> SEQUENCE: 2

Met Glu Asn Ile Thr Ser Gly Phe Leu Gly Pro Leu Leu Val Leu Gln
1               5                   10                  15

Ala Gly Phe Phe
            20

<210> SEQ ID NO 3
<211> LENGTH: 20
<212> TYPE: PRT
<213> ORGANISM: Hepatitis B virus

<400> SEQUENCE: 3

Met Glu Asn Ile Ala Ser Gly Leu Leu Gly Pro Leu Leu Val Leu Gln
1               5                   10                  15

```
Ala Gly Phe Phe
            20

<210> SEQ ID NO 4
<211> LENGTH: 20
<212> TYPE: PRT
<213> ORGANISM: Hepatitis B virus

<400> SEQUENCE: 4

Met Glu Asn Thr Thr Ser Gly Phe Leu Gly Pro Leu Leu Val Leu Gln
1               5                  10                  15

Ala Gly Phe Phe
            20

<210> SEQ ID NO 5
<211> LENGTH: 20
<212> TYPE: PRT
<213> ORGANISM: Hepatitis B virus

<400> SEQUENCE: 5

Met Glu Ser Thr Thr Ser Gly Phe Leu Gly Pro Leu Leu Val Leu Gln
1               5                  10                  15

Ala Gly Phe Phe
            20

<210> SEQ ID NO 6
<211> LENGTH: 20
<212> TYPE: PRT
<213> ORGANISM: Hepatitis B virus

<400> SEQUENCE: 6

Pro Leu Leu Val Leu Gln Ala Gly Phe Phe Leu Leu Thr Arg Ile Leu
1               5                  10                  15

Thr Ile Pro Gln
            20

<210> SEQ ID NO 7
<211> LENGTH: 20
<212> TYPE: PRT
<213> ORGANISM: Hepatitis B virus

<400> SEQUENCE: 7

Pro Leu Leu Val Leu Gln Ala Gly Phe Phe Leu Leu Thr Lys Ile Leu
1               5                  10                  15

Thr Ile Pro Gln
            20

<210> SEQ ID NO 8
<211> LENGTH: 20
<212> TYPE: PRT
<213> ORGANISM: Hepatitis B virus

<400> SEQUENCE: 8

Leu Leu Thr Arg Ile Leu Thr Ile Pro Gln Ser Leu Asp Ser Trp Trp
1               5                  10                  15

Thr Ser Leu Asn
            20

<210> SEQ ID NO 9
<211> LENGTH: 20
<212> TYPE: PRT
<213> ORGANISM: Hepatitis B virus
```

```
<400> SEQUENCE: 9

Ser Leu Asp Ser Trp Trp Thr Ser Leu Asn Phe Leu Gly Gly Ser Pro
1               5                   10                  15

Val Cys Leu Gly
            20

<210> SEQ ID NO 10
<211> LENGTH: 20
<212> TYPE: PRT
<213> ORGANISM: Hepatitis B virus

<400> SEQUENCE: 10

Ser Leu Asp Ser Trp Trp Thr Ser Leu Asn Phe Leu Gly Gly Thr Pro
1               5                   10                  15

Val Cys Leu Gly
            20

<210> SEQ ID NO 11
<211> LENGTH: 20
<212> TYPE: PRT
<213> ORGANISM: Hepatitis B virus

<400> SEQUENCE: 11

Ser Leu Asp Ser Trp Trp Thr Ser Leu Asn Phe Leu Gly Gly Ala Pro
1               5                   10                  15

Thr Cys Pro Gly
            20

<210> SEQ ID NO 12
<211> LENGTH: 20
<212> TYPE: PRT
<213> ORGANISM: Hepatitis B virus

<400> SEQUENCE: 12

Ser Leu Asp Ser Trp Trp Thr Ser Leu Asn Phe Leu Gly Gly Thr Thr
1               5                   10                  15

Val Cys Leu Gly
            20

<210> SEQ ID NO 13
<211> LENGTH: 20
<212> TYPE: PRT
<213> ORGANISM: Hepatitis B virus

<400> SEQUENCE: 13

Phe Leu Gly Gly Ser Pro Val Cys Leu Gly Gln Asn Ser Gln Ser Pro
1               5                   10                  15

Thr Ser Asn His
            20

<210> SEQ ID NO 14
<211> LENGTH: 20
<212> TYPE: PRT
<213> ORGANISM: Hepatitis B virus

<400> SEQUENCE: 14

Phe Leu Gly Gly Thr Pro Val Cys Leu Gly Gln Asn Ser Gln Ser Gln
1               5                   10                  15

Ile Ser Ser His
            20
```

```
<210> SEQ ID NO 15
<211> LENGTH: 20
<212> TYPE: PRT
<213> ORGANISM: Hepatitis B virus

<400> SEQUENCE: 15

Phe Leu Gly Gly Ala Pro Thr Cys Pro Gly Gln Asn Ser Gln Ser Pro
1               5                   10                  15

Thr Ser Asn His
            20

<210> SEQ ID NO 16
<211> LENGTH: 20
<212> TYPE: PRT
<213> ORGANISM: Hepatitis B virus

<400> SEQUENCE: 16

Phe Leu Gly Gly Thr Thr Val Cys Leu Gly Gln Asn Ser Gln Ser Pro
1               5                   10                  15

Thr Ser Asn His
            20

<210> SEQ ID NO 17
<211> LENGTH: 19
<212> TYPE: PRT
<213> ORGANISM: Hepatitis B virus

<400> SEQUENCE: 17

Gln Asn Ser Gln Ser Pro Thr Ser Asn His Ser Pro Thr Ser Cys Pro
1               5                   10                  15

Pro Ile Cys

<210> SEQ ID NO 18
<211> LENGTH: 19
<212> TYPE: PRT
<213> ORGANISM: Hepatitis B virus

<400> SEQUENCE: 18

Gln Asn Ser Gln Ser Gln Ile Ser Ser His Ser Pro Thr Cys Cys Pro
1               5                   10                  15

Pro Ile Cys

<210> SEQ ID NO 19
<211> LENGTH: 20
<212> TYPE: PRT
<213> ORGANISM: Hepatitis B virus

<400> SEQUENCE: 19

Ser Pro Thr Ser Cys Pro Pro Ile Cys Pro Gly Tyr Arg Trp Met Cys
1               5                   10                  15

Leu Arg Arg Phe
            20

<210> SEQ ID NO 20
<211> LENGTH: 20
<212> TYPE: PRT
<213> ORGANISM: Hepatitis B virus

<400> SEQUENCE: 20

Ser Pro Thr Ser Cys Pro Pro Thr Cys Pro Gly Tyr Arg Trp Met Cys
1               5                   10                  15
```

Leu Arg Arg Phe
        20

<210> SEQ ID NO 21
<211> LENGTH: 20
<212> TYPE: PRT
<213> ORGANISM: Hepatitis B virus

<400> SEQUENCE: 21

Gly Tyr Arg Trp Met Cys Leu Arg Arg Phe Ile Ile Phe Leu Phe Ile
1               5                   10                  15

Leu Leu Leu Cys
        20

<210> SEQ ID NO 22
<211> LENGTH: 20
<212> TYPE: PRT
<213> ORGANISM: Hepatitis B virus

<400> SEQUENCE: 22

Gly Tyr Arg Trp Met Cys Leu Arg Arg Phe Ile Ile Phe Leu Cys Ile
1               5                   10                  15

Leu Leu Leu Cys
        20

<210> SEQ ID NO 23
<211> LENGTH: 20
<212> TYPE: PRT
<213> ORGANISM: Hepatitis B virus

<400> SEQUENCE: 23

Ile Ile Phe Leu Phe Ile Leu Leu Leu Cys Leu Ile Phe Leu Ile Val
1               5                   10                  15

Leu Leu Asp Tyr
        20

<210> SEQ ID NO 24
<211> LENGTH: 20
<212> TYPE: PRT
<213> ORGANISM: Hepatitis B virus

<400> SEQUENCE: 24

Leu Ile Phe Leu Leu Val Leu Leu Asp Tyr Gln Gly Met Leu Pro Val
1               5                   10                  15

Cys Pro Leu Leu
        20

<210> SEQ ID NO 25
<211> LENGTH: 19
<212> TYPE: PRT
<213> ORGANISM: Hepatitis B virus

<400> SEQUENCE: 25

Gln Gly Met Leu Pro Val Cys Pro Leu Ile Pro Gly Ser Thr Thr Thr
1               5                   10                  15

Ser Thr Gly

<210> SEQ ID NO 26
<211> LENGTH: 19
<212> TYPE: PRT
<213> ORGANISM: Hepatitis B virus

<400> SEQUENCE: 26

Gln Gly Met Leu Pro Val Cys Pro Leu Ile Pro Gly Ser Ser Thr Thr
1               5                   10                  15

Ser Thr Gly

<210> SEQ ID NO 27
<211> LENGTH: 19
<212> TYPE: PRT
<213> ORGANISM: Hepatitis B virus

<400> SEQUENCE: 27

Gln Gly Met Leu Pro Val Cys Pro Leu Leu Pro Gly Thr Ser Thr Thr
1               5                   10                  15

Ser Thr Gly

<210> SEQ ID NO 28
<211> LENGTH: 20
<212> TYPE: PRT
<213> ORGANISM: Hepatitis B virus

<400> SEQUENCE: 28

Pro Gly Ser Thr Thr Thr Ser Thr Gly Pro Cys Lys Thr Cys Thr Thr
1               5                   10                  15

Pro Ala Gln Gly
            20

<210> SEQ ID NO 29
<211> LENGTH: 20
<212> TYPE: PRT
<213> ORGANISM: Hepatitis B virus

<400> SEQUENCE: 29

Pro Gly Thr Ser Thr Thr Ser Thr Gly Pro Cys Lys Thr Cys Thr Ile
1               5                   10                  15

Pro Ala Gln Gly
            20

<210> SEQ ID NO 30
<211> LENGTH: 20
<212> TYPE: PRT
<213> ORGANISM: Hepatitis B virus

<400> SEQUENCE: 30

Pro Gly Ser Ser Thr Thr Ser Thr Gly Pro Cys Arg Thr Cys Thr Thr
1               5                   10                  15

Pro Ala Gln Gly
            20

<210> SEQ ID NO 31
<211> LENGTH: 20
<212> TYPE: PRT
<213> ORGANISM: Hepatitis B virus

<400> SEQUENCE: 31

Pro Gly Ser Ser Thr Thr Ser Thr Gly Pro Cys Arg Thr Cys Met Thr
1               5                   10                  15

Thr Ala Gln Gly
            20

<210> SEQ ID NO 32
<211> LENGTH: 20
<212> TYPE: PRT

<213> ORGANISM: Hepatitis B virus

<400> SEQUENCE: 32

Cys Lys Thr Cys Thr Thr Pro Ala Gln Gly Asn Ser Met Phe Pro Ser
1 5 10 15

Cys Cys Cys Thr
20

<210> SEQ ID NO 33
<211> LENGTH: 20
<212> TYPE: PRT
<213> ORGANISM: Hepatitis B virus

<400> SEQUENCE: 33

Cys Lys Thr Cys Thr Thr Pro Ala Gln Gly Thr Ser Met Phe Pro Ser
1 5 10 15

Cys Cys Cys Thr
20

<210> SEQ ID NO 34
<211> LENGTH: 20
<212> TYPE: PRT
<213> ORGANISM: Hepatitis B virus

<400> SEQUENCE: 34

Cys Lys Thr Cys Thr Ile Pro Ala Gln Gly Thr Ser Met Phe Pro Ser
1 5 10 15

Cys Cys Cys Thr
20

<210> SEQ ID NO 35
<211> LENGTH: 20
<212> TYPE: PRT
<213> ORGANISM: Hepatitis B virus

<400> SEQUENCE: 35

Cys Arg Thr Cys Thr Thr Pro Ala Gln Gly Thr Ser Met Tyr Pro Ser
1 5 10 15

Cys Cys Cys Thr
20

<210> SEQ ID NO 36
<211> LENGTH: 20
<212> TYPE: PRT
<213> ORGANISM: Hepatitis B virus

<400> SEQUENCE: 36

Cys Arg Thr Cys Met Thr Thr Ala Gln Gly Thr Ser Met Tyr Pro Ser
1 5 10 15

Cys Cys Cys Thr
20

<210> SEQ ID NO 37
<211> LENGTH: 20
<212> TYPE: PRT
<213> ORGANISM: Hepatitis B virus

<400> SEQUENCE: 37

Asn Ser Met Phe Pro Ser Cys Cys Cys Thr Lys Pro Thr Asp Gly Asn
1 5 10 15

Cys Thr Cys Ile
20

<210> SEQ ID NO 38
<211> LENGTH: 20
<212> TYPE: PRT
<213> ORGANISM: Hepatitis B virus

<400> SEQUENCE: 38

Thr Ser Met Phe Pro Ser Cys Cys Cys Thr Lys Pro Ser Asp Gly Asn
1               5                   10                  15

Cys Thr Cys Ile
            20

<210> SEQ ID NO 39
<211> LENGTH: 20
<212> TYPE: PRT
<213> ORGANISM: Hepatitis B virus

<400> SEQUENCE: 39

Lys Pro Ser Asp Gly Asn Cys Thr Cys Ile Pro Ile Pro Ser Ser Trp
1               5                   10                  15

Ala Phe Ala Arg
            20

<210> SEQ ID NO 40
<211> LENGTH: 20
<212> TYPE: PRT
<213> ORGANISM: Hepatitis B virus

<400> SEQUENCE: 40

Pro Ile Pro Ser Ser Trp Ala Phe Ala Lys Tyr Leu Trp Glu Trp Ala
1               5                   10                  15

Ser Val Arg Phe
            20

<210> SEQ ID NO 41
<211> LENGTH: 20
<212> TYPE: PRT
<213> ORGANISM: Hepatitis B virus

<400> SEQUENCE: 41

Pro Ile Pro Ser Ser Trp Ala Phe Ala Lys Phe Leu Trp Glu Trp Ala
1               5                   10                  15

Ser Val Arg Phe
            20

<210> SEQ ID NO 42
<211> LENGTH: 20
<212> TYPE: PRT
<213> ORGANISM: Hepatitis B virus

<400> SEQUENCE: 42

Pro Ile Pro Ser Ser Trp Ala Phe Ala Arg Phe Leu Trp Glu Trp Ala
1               5                   10                  15

Ser Val Arg Phe
            20

<210> SEQ ID NO 43
<211> LENGTH: 20
<212> TYPE: PRT
<213> ORGANISM: Hepatitis B virus

<400> SEQUENCE: 43

Pro Ile Pro Ser Ser Trp Ala Phe Gly Lys Phe Leu Trp Glu Trp Ala
1               5                   10                  15

Ser Ala Arg Phe
            20

<210> SEQ ID NO 44
<211> LENGTH: 20
<212> TYPE: PRT
<213> ORGANISM: Hepatitis B virus

<400> SEQUENCE: 44

Phe Leu Trp Glu Trp Ala Ser Val Arg Phe Ser Trp Leu Ser Leu Leu
1               5                   10                  15

Val Pro Phe Val
            20

<210> SEQ ID NO 45
<211> LENGTH: 20
<212> TYPE: PRT
<213> ORGANISM: Hepatitis B virus

<400> SEQUENCE: 45

Phe Leu Trp Glu Trp Ala Ser Ala Arg Phe Ser Trp Leu Ser Leu Leu
1               5                   10                  15

Val Pro Phe Val
            20

<210> SEQ ID NO 46
<211> LENGTH: 20
<212> TYPE: PRT
<213> ORGANISM: Hepatitis B virus

<400> SEQUENCE: 46

Ser Trp Leu Ser Leu Leu Val Pro Phe Val Gln Trp Phe Val Gly Leu
1               5                   10                  15

Ser Pro Thr Val
            20

<210> SEQ ID NO 47
<211> LENGTH: 20
<212> TYPE: PRT
<213> ORGANISM: Hepatitis B virus

<400> SEQUENCE: 47

Ser Trp Leu Ser Leu Leu Val Pro Phe Val Gln Trp Phe Ala Gly Leu
1               5                   10                  15

Ser Pro Thr Val
            20

<210> SEQ ID NO 48
<211> LENGTH: 20
<212> TYPE: PRT
<213> ORGANISM: Hepatitis B virus

<400> SEQUENCE: 48

Gln Trp Phe Val Gly Leu Ser Pro Thr Val Trp Leu Ser Ala Ile Trp
1               5                   10                  15

Met Met Trp Tyr
            20

<210> SEQ ID NO 49
<211> LENGTH: 20

```
<212> TYPE: PRT
<213> ORGANISM: Hepatitis B virus

<400> SEQUENCE: 49

Gln Trp Phe Ala Gly Leu Ser Pro Thr Val Trp Leu Ser Val Ile Trp
1               5                   10                  15

Met Met Trp Tyr
            20

<210> SEQ ID NO 50
<211> LENGTH: 20
<212> TYPE: PRT
<213> ORGANISM: Hepatitis B virus

<400> SEQUENCE: 50

Trp Leu Ser Ala Ile Trp Met Met Trp Tyr Trp Gly Pro Ser Leu Tyr
1               5                   10                  15

Ser Ile Val Ser
            20

<210> SEQ ID NO 51
<211> LENGTH: 20
<212> TYPE: PRT
<213> ORGANISM: Hepatitis B virus

<400> SEQUENCE: 51

Trp Leu Ser Val Ile Trp Met Met Trp Phe Trp Gly Pro Ser Leu Tyr
1               5                   10                  15

Asn Ile Leu Ser
            20

<210> SEQ ID NO 52
<211> LENGTH: 20
<212> TYPE: PRT
<213> ORGANISM: Hepatitis B virus

<400> SEQUENCE: 52

Trp Leu Ser Val Ile Trp Met Met Trp Tyr Trp Gly Pro Ser Leu Tyr
1               5                   10                  15

Asn Ile Leu Ser
            20

<210> SEQ ID NO 53
<211> LENGTH: 20
<212> TYPE: PRT
<213> ORGANISM: Hepatitis B virus

<400> SEQUENCE: 53

Trp Gly Pro Ser Leu Tyr Ser Ile Val Ser Pro Phe Ile Pro Leu Leu
1               5                   10                  15

Pro Ile Phe Phe
            20

<210> SEQ ID NO 54
<211> LENGTH: 20
<212> TYPE: PRT
<213> ORGANISM: Hepatitis B virus

<400> SEQUENCE: 54

Trp Gly Pro Ser Leu Tyr Asn Ile Leu Ser Pro Phe Met Pro Leu Leu
1               5                   10                  15

Pro Ile Phe Phe
```

```
<210> SEQ ID NO 55
<211> LENGTH: 20
<212> TYPE: PRT
<213> ORGANISM: Hepatitis B virus

<400> SEQUENCE: 55

Trp Gly Pro Ser Leu Tyr Asn Ile Leu Ser Pro Phe Leu Pro Leu Leu
1               5                   10                  15

Pro Ile Phe Phe
            20

<210> SEQ ID NO 56
<211> LENGTH: 20
<212> TYPE: PRT
<213> ORGANISM: Hepatitis B virus

<400> SEQUENCE: 56

Trp Gly Pro Ser Leu Tyr Ser Ile Leu Ser Pro Phe Leu Pro Leu Leu
1               5                   10                  15

Pro Ile Phe Phe
            20

<210> SEQ ID NO 57
<211> LENGTH: 16
<212> TYPE: PRT
<213> ORGANISM: Hepatitis B virus

<400> SEQUENCE: 57

Pro Phe Leu Pro Leu Leu Pro Ile Phe Phe Cys Leu Trp Val Tyr Ile
1               5                   10                  15
```